US007088799B2

(12) United States Patent
Hoffman

(10) Patent No.: US 7,088,799 B2
(45) Date of Patent: *Aug. 8, 2006

(54) METHOD AND APPARATUS FOR PRESENTING MULTIPLE PRE-SUBJECT FILTERING PROFILES DURING CT DATA ACQUISITION

(75) Inventor: David M. Hoffman, New Berlin, WI (US)

(73) Assignee: General Electric Company, Schenectady, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/160,830

(22) Filed: Jul. 12, 2005

(65) Prior Publication Data
US 2005/0243971 A1 Nov. 3, 2005

Related U.S. Application Data

(63) Continuation of application No. 10/249,931, filed on May 20, 2003, now Pat. No. 6,968,030.

(51) Int. Cl.
*G21K 3/00* (2006.01)
(52) U.S. Cl. .............................. 378/5; 378/16; 378/98.9; 378/158; 378/159
(58) Field of Classification Search .................. 378/5, 378/9, 16, 57, 98.9, 98.11, 156–159, 147–151, 378/7
See application file for complete search history.

(56) References Cited

U.S. PATENT DOCUMENTS

| 4,277,685 | A | * | 7/1981 | Covic et al. ..................... 378/7 |
| 4,399,550 | A | * | 8/1983 | Hauck et al. ................... 378/5 |
| 4,679,221 | A | * | 7/1987 | O'Brien et al. ............. 378/148 |
| 4,947,417 | A | | 8/1990 | Hartwell ..................... 378/147 |
| 5,129,740 | A | * | 7/1992 | Matsushita et al. ......... 384/441 |
| 5,301,108 | A | | 4/1994 | Hsieh ............................. 378/8 |
| 5,396,889 | A | | 3/1995 | Ueda et al. ................. 600/407 |
| 5,485,492 | A | | 1/1996 | Pelc ............................... 378/5 |
| 5,568,533 | A | | 10/1996 | Kumazaki et al. .......... 378/156 |
| 5,661,774 | A | | 8/1997 | Gordon et al. ............. 378/101 |
| 5,838,758 | A | * | 11/1998 | Krug et al. ................... 378/53 |
| 5,982,846 | A | | 11/1999 | Toth et al. ..................... 378/19 |
| 6,226,352 | B1 | | 5/2001 | Salb ........................... 378/98.9 |
| 6,307,918 | B1 | | 10/2001 | Toth et al. ................... 378/158 |
| 6,404,841 | B1 | | 6/2002 | Pforr et al. ..................... 378/4 |
| 6,487,274 | B1 | * | 11/2002 | Bertsche ..................... 378/143 |
| 6,597,758 | B1 | | 7/2003 | Rosner ......................... 378/53 |
| 6,614,878 | B1 | | 9/2003 | Bogatu et al. .............. 378/158 |
| 2003/0195416 | A1 | * | 10/2003 | Toth ............................ 600/427 |

* cited by examiner

*Primary Examiner*—Allen C. Ho
(74) *Attorney, Agent, or Firm*—Ziolkowski Patent Solutions Group, SC; Michael A. Della Penna; Carl B. Horton

(57) ABSTRACT

The present invention is directed to a method and apparatus for CT data acquisition using a rotatable pre-subject filter having more than one filtering profile to control radiation exposure to a subject. The filter is caused to rotate by a motor and bearing assembly and has one profile used to filter radiation when the radiation source is positioned above a subject and another profile that is used to filter radiation when the radiation source is positioned at a side of the subject.

20 Claims, 6 Drawing Sheets

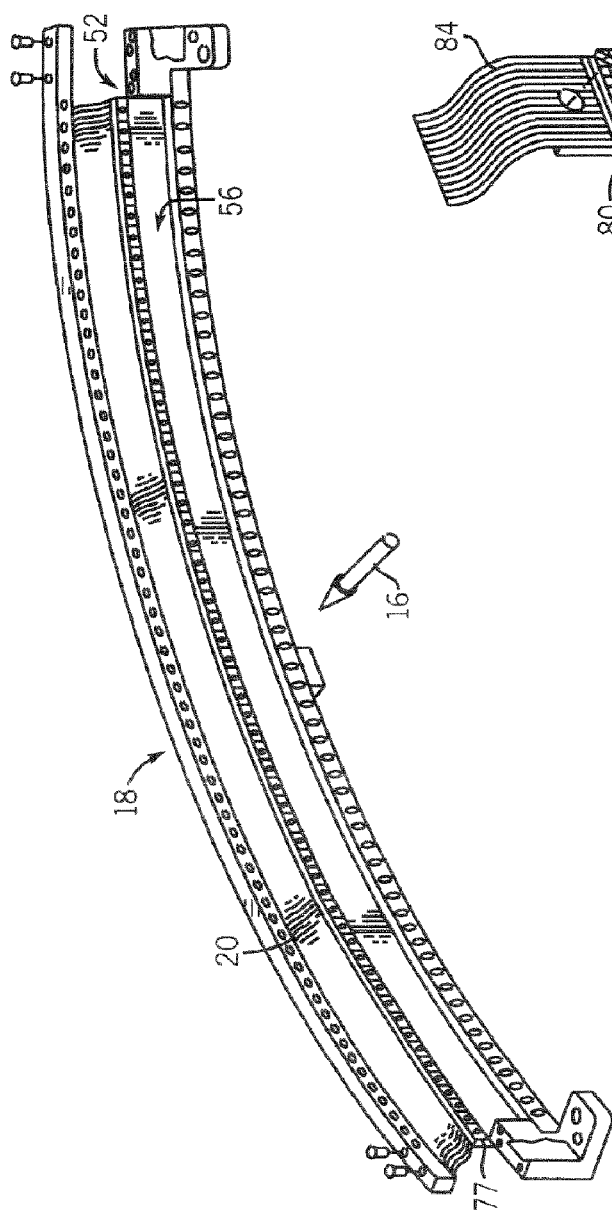
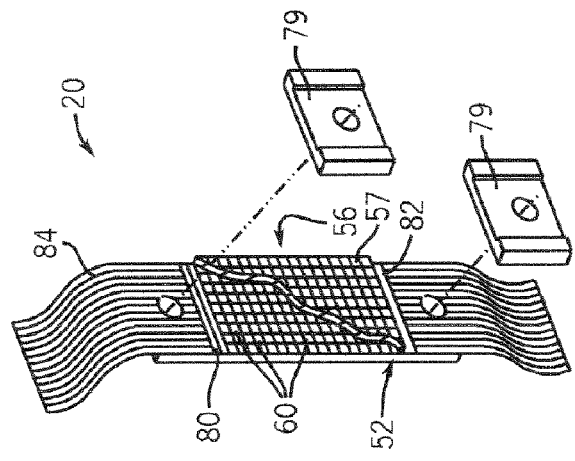
FIG. 3
FIG. 4

METHOD AND APPARATUS FOR PRESENTING MULTIPLE PRE-SUBJECT FILTERING PROFILES DURING CT DATA ACQUISITION

CROSS-REFERENCE TO RELATED APPLICATION

The present invention is a continuation and claims priority of U.S. Ser. No. 10/249,931, filed May 20, 2003 now U.S. Pat. No. 6,968,030.

BACKGROUND OF THE INVENTION

The present invention relates generally to diagnostic imaging and, more particularly, to a method and apparatus of dynamically filtering radiation emitted toward a subject during radiographic imaging.

Typically, in radiographic imaging systems, an x-ray source emits x-rays toward a subject or object, such as a patient or a piece of luggage. Hereinafter, the terms "subject" and "object" may be interchangeably used to describe anything capable of being imaged. The beam, after being attenuated by the subject, impinges upon an array of radiation detectors. The intensity of the attenuated beam radiation received at the detector array is typically dependent upon the attenuation of the x-rays. Each detector element of the detector array produces a separate electrical signal indicative of the attenuated beam received by each detector element. The electrical signals are transmitted to a data processing system for analysis which ultimately produces an image.

In computed tomography (CT) imaging systems, the x-ray source and the detector array are rotated about a gantry within an imaging plane and around the subject. X-ray sources typically include x-ray tubes, which emit the x-rays as a beam at a focal point. X-ray detectors typically include a collimator for collimating x-ray beams received at the detector, a scintillator for converting x-rays to light energy adjacent the collimator, and a photodiode for receiving the light energy from an adjacent scintillator and producing electrical signals therefrom. Typically, each scintillator of a scintillator array converts x-rays to light energy. Each photodiode detects the light energy and generates a corresponding electrical signal. The outputs of the photodiodes are then transmitted to the data processing system for image reconstruction.

There is increasingly a need to reduce radiation dosage projected toward a subject during an imaging session. It is generally well known that significant dose reduction may be achieved by using a "bowtie" filter to shape the intensity profile of an x-ray beam. Surface dose reductions may be as much as 50% using a bowtie filter. Generally, the bowtie filter is constructed such that the profile used to filter the radiation projected toward the subject is constant through the imaging process. That is, the bowtie filter is constructed to filter radiation emitted toward a subject such that the sum of the radiation path length through the filter plus the path length through the subject is roughly constant. One drawback of this construction is that a subject's shape is not constant. For example, a patient's shape changes as a function of view angle as the x-ray tube and detector rotate around the patient and because the filter has a constant filtering profile at different points in the imaging process, portions of the subject may be over-radiated whereas at other times, other portions will be under-radiated. As a result, a choice must be made between having under-radiated portions during the imaging process or increasing the dosage such that a minimum radiation dosage throughout the imaging session is maintained with some portion being over-radiated.

A number of developments have been made to address this situation. The CT scanner may be equipped with multiple beam shaping filters. Multiple filters, however, increases the manufacturing costs of the CT scanner as well as requiring additional controls to insure the appropriate filters are being used during the scan session. Another approach is to dynamically control the amount of x-ray dosage emitted by the projection source as a function of view angle. This approach, however, requires significant and complex controls to alter the amount of radiation projected toward the subject during the scan that significantly increases the costs of the CT system nor takes into account shape of the pre-patient filter.

Therefore, it would be desirable to design a pre-subject filter having a filter that rotates and effectively changes its filtering and been shaping properties as a function of view angle as the x-ray tube and detector rotate around a subject.

BRIEF DESCRIPTION OF THE INVENTION

The present invention is a directed method and apparatus for CT data acquisition using a rotatable pre-subject filter having multiple filtering profiles to dynamically control radiation exposure to a subject that overcomes the aforementioned drawbacks. Specifically, a filter is disclosed that is shaped to have varying filtering profiles. The filter is designed to rotate about its lengthwise axis such that the filtering profile used may be varied as a function of the view angle of the projection source.

Therefore, in accordance with one aspect, the present invention includes a pre-subject filter assembly for a CT imaging system having a detector assembly and a high frequency electromagnetic energy projection source configured to rotate about a subject during an imaging session. The filter assembly includes a beam shaping filter having a generally cylindrical shaped body defining multiple filtering profiles. The filter is constructed to rotate about an axis of rotation that extends through the body. A controller is provided to cause rotation of the filter about the axis of rotation during an imaging session to dynamically filter high frequency electromagnetic energy projected toward the subject as a function of view angle.

In accordance with another aspect, a CT system includes a rotatable gantry having an opening to receive a subject to be scanned. A moveable high frequency electromagnetic energy projection source projects high frequency electromagnetic energy such as x-rays toward the subject at least two view angles during an imaging session. A pre-subject includes a filter that is rotatable about itself relative to an axis of rotation extending the filter during the imaging session. The filter includes multiple filtering profiles. As such, the filter moves circumferentially around the subject during the imaging session but also rotates or spins relative to itself during the imaging session such that multiple filtering profiles are usable during the imaging session. The CT system further includes a scintillator array and a photodiode array that rotate synchronously with the filter and x-ray source during the imaging session. The scintillator and photodiode arrays collectively form a detector array that detects x-rays attenuated by the subject during the imaging session and outputs electrical signals indicative of the attenuation. The detector output is then input to a DAS configured to reconstruct an image of the subject. The CT system further includes a computer programmed to rotate the filter about the axis of rotation such that a first view angle a first filtering profile is presented and at a second view angle a second filtering profile is presented.

In accordance with yet another aspect of the present invention, a method of reducing x-ray exposure during CT data acquisition includes positioning a subject to be scanned in a scanning bay and projecting x-rays toward the subject from an x-ray source at a first view angle. A first profile of a multi-profile filter is then positioned between the x-ray source and the subject when the x-ray source is projecting x-rays at the first view angle. The x-ray source is then rotated to a second view angle and projects x-rays toward the subject therefrom. Simultaneously therewith, the multi-profile filter is caused to rotate about an axis of rotation that extends through a length of the filter such that a second profile is positioned between the x-ray source and the subject when the x-ray source is projecting x-rays from the second view angle.

Various other features, objects and advantages of the present invention will be made apparent from the following detailed description and the drawings.

BRIEF DESCRIPTION OF THE DRAWINGS

The drawings illustrate one preferred embodiment presently contemplated for carrying out the invention.

In the drawings:

FIG. 3 is a perspective view of one embodiment of a CT system detector array.

FIG. 4 is a perspective view of one embodiment of a detector.

DETAILED DESCRIPTION OF THE PREFERRED EMBODIMENT

Figure 1:
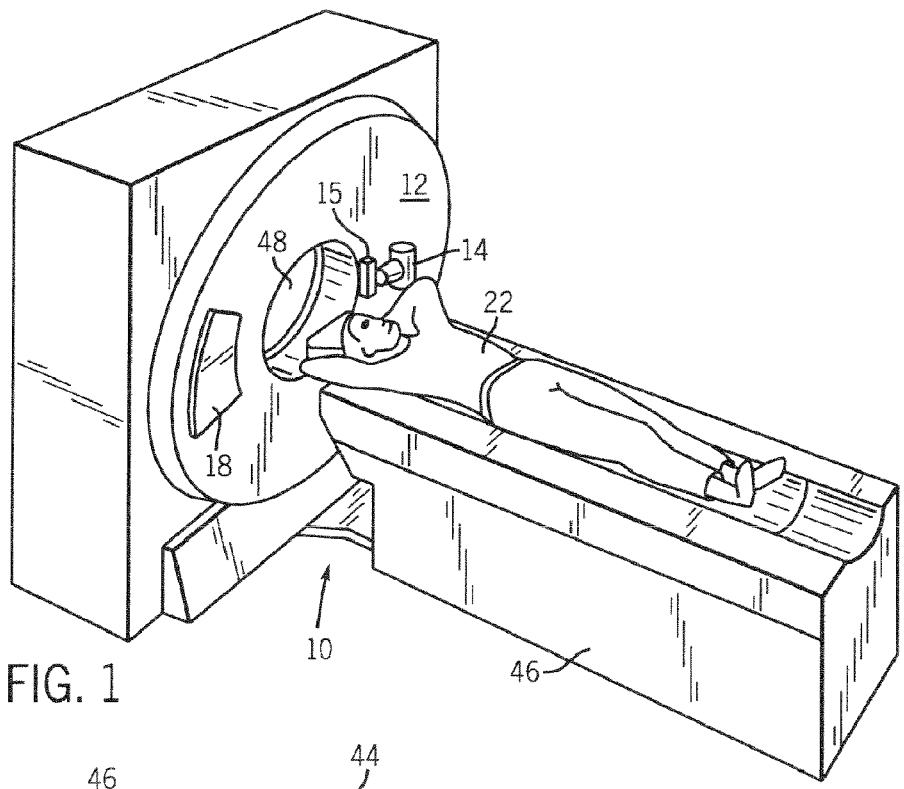
FIG. 1 is a pictorial view of a CT imaging system.
Figure 2:
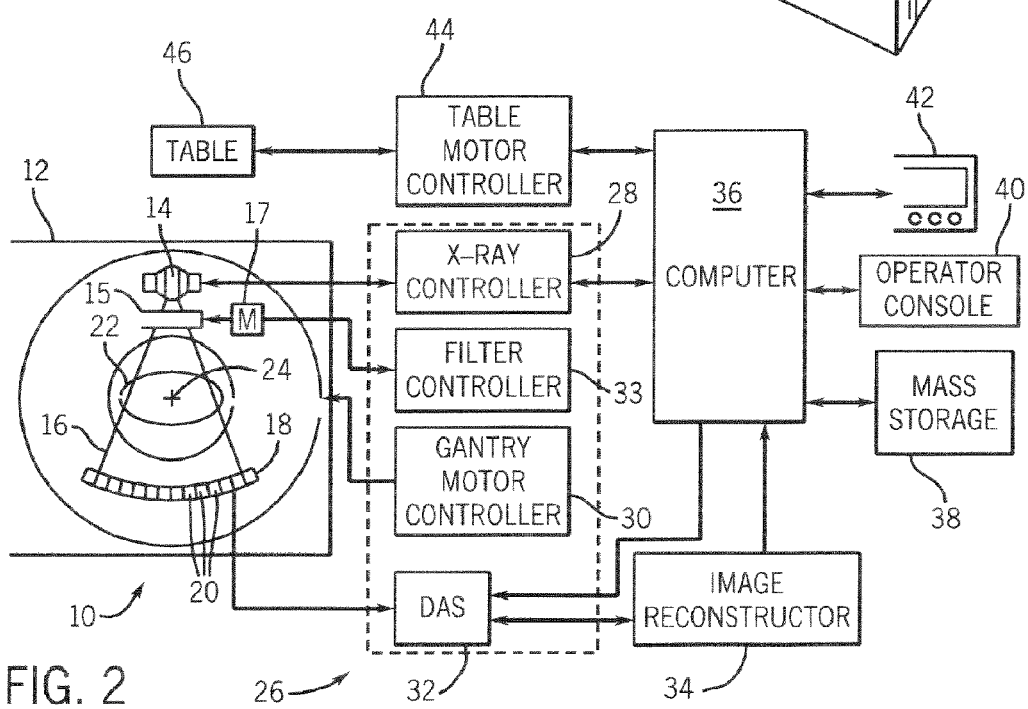
FIG. 2 is a block schematic diagram of the system illustrated in FIG. 1.

The present invention is described with respect to a radiographic imaging system such as the CT system shown in FIGS. 1–2. However, it will be appreciated by those skilled in the art that the present invention is equally applicable for use with other radiographic imaging systems utilizing a rotating projection source and a pre-subject filter Moreover, the present invention will be described with respect to the emission and detection of x-rays. However, one skilled in the art will further appreciate, that the present invention is equally applicable for the emission and detection of other high frequency electromagnetic energy.

Referring to FIGS. 1 and 2, a "third generation" CT imaging system 10 is shown as including a gantry 12. The present invention, however, is applicable with other CT systems. Gantry 12 has an x-ray source 14 that projects a beam of x-rays 16 through filter 15 toward a detector array 18 on the opposite side of the gantry 12. Detector array 18 is formed by a plurality of detectors 20 which together sense the projected x-rays that pass through a medical patient 22. Each detector 20 produces an electrical signal that represents the intensity of an impinging x-ray beam and hence the attenuated beam as it passes through the patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to an x-ray source 14, a gantry motor controller 30 that controls the rotational speed and position of gantry 12, and filter controller 33 that controls filter 15. As will be described in greater detail below, filter 15 is rotated or caused to spin about a lengthwise axis of rotation by motor assembly 17. A data acquisition system (DAS) 32 in control mechanism 26 samples analog data from detectors 20 and converts the data to digital signals for subsequent processing. An image reconstructor 34 receives sampled and digitized x-ray data from DAS 32 and performs high speed reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 and gantry 12. Particularly, table 46 moves portions of patient 22 through a gantry opening 48.

As shown in FIGS. 3 and 4, detector array 18 includes a plurality of scintillators 57 forming a scintillator array 56. A collimator (not shown) is positioned above scintillator array 56 to collimate x-ray beams 16 before such beams impinge upon scintillator array 56.

In one embodiment, shown in FIG. 3, detector array 18 includes 57 detectors 20, each detector 20 having an array size of 16×16. As a result, array 18 has 16 rows and 912 columns (16×57 detectors) which allows 16 simultaneous slices of data to be collected with each rotation of gantry 12.

Switch arrays 80 and 82, FIG. 4, are multi-dimensional semiconductor arrays coupled between scintillator array 56 and DAS 32. Switch arrays 80 and 82 include a plurality of field effect transistors (FET) (not shown) arranged as multi-dimensional array. The FET array includes a number of electrical leads connected to each of the respective photodiodes 60 and a number of output leads electrically connected to DAS 32 via a flexible electrical interface 84. Particularly, about one-half of photodiode outputs are electrically connected to switch 80 with the other one-half of photodiode outputs electrically connected to switch 82. Additionally, a reflector layer (not shown) may be interposed between each scintillator 57 to reduce light scattering from adjacent scintillators. Each detector 20 is secured to a detector frame 77, FIG. 3, by mounting brackets 79.

Switch arrays 80 and 82 further include a decoder (not shown) that enables, disables, or combines photodiode outputs in accordance with a desired number of slices and slice resolutions for each slice. Decoder, in one embodiment, is a decoder chip or a FET controller as known in the art.

Decoder includes a plurality of output and control lines coupled to switch arrays 80 and 82 and DAS 32. In one embodiment defined as a 16 slice mode, decoder enables switch arrays 80 and 82 so that all rows of the photodiode array 52 are activated, resulting in 16 simultaneous slices of data for processing by DAS 32. Of course, many other slice combinations are possible. For example, decoder may also select from other slice modes, including one, two, and four-slice modes.

Figure 5:
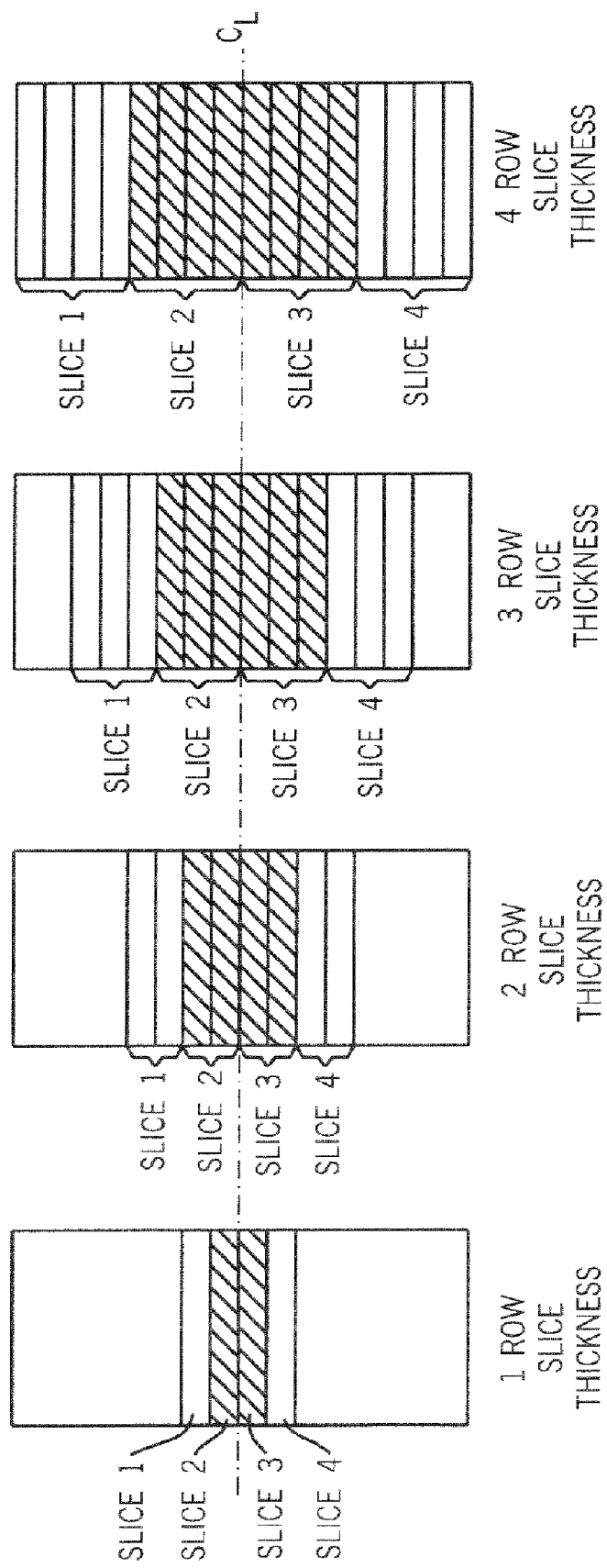
FIG. 5 is illustrative of various configurations of the detector in FIG. 4 in a four-slice mode.

As shown in FIG. 5, by transmitting the appropriate decoder instructions, switch arrays 80 and 82 can be configured in the four-slice mode so that the data is collected from four slices of one or more rows of photodiode array 52. Depending upon the specific configuration of switch arrays 80 and 82, various combinations of photodiodes 60 can be enabled, disabled, or combined so that the slice thickness may consist of one, two, three, or four rows of scintillator array elements 57. Additional examples include, a single slice mode including one slice with slices ranging from 1.25 mm thick to 20 mm thick, and a two slice mode including two slices with slices ranging from 1.25 mm thick to 10 mm thick. Additional modes beyond those described are contemplated.

Figure 6:
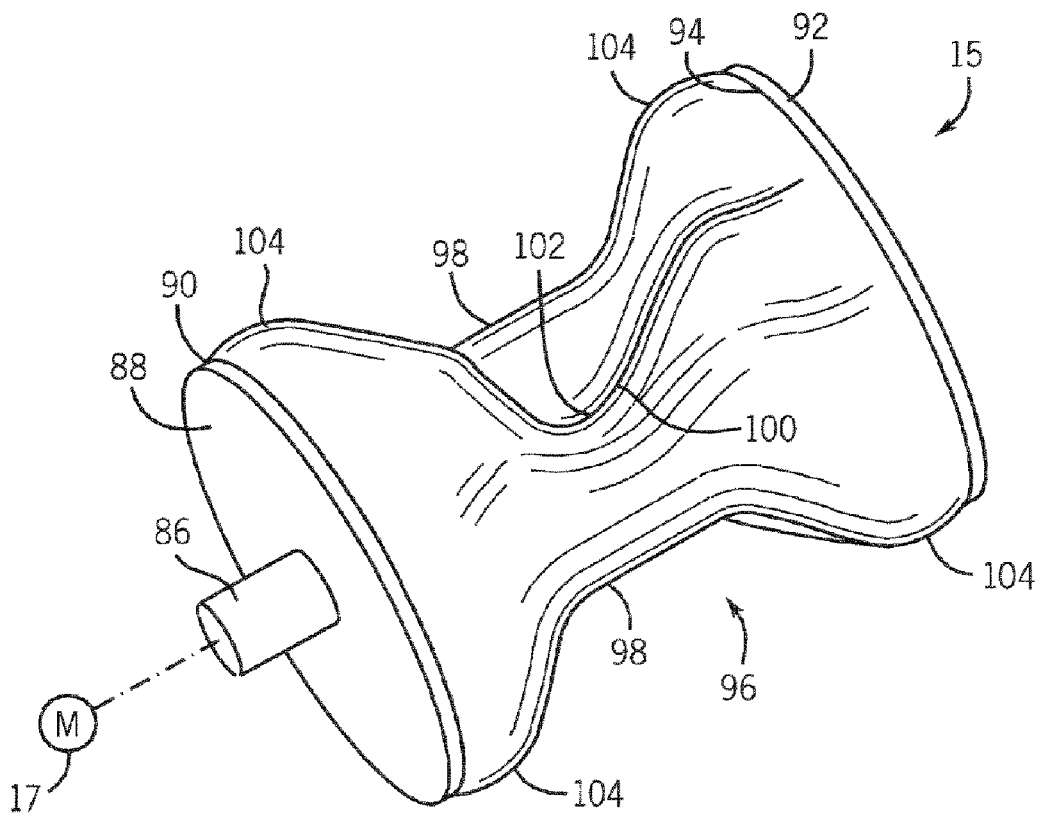
FIG. 6 is a perspective view of a rotatable pre-patient filter assembly in accordance with the present invention.

Referring now to FIG. 6, a statically shaped pre-patient filter 15 is shown in perspective as being connectable to a motor or other drive assembly 17 via a shaft 86 that is operationally connected to the filter 15 via end cap or plate 88. End cap 88 is designed to be adhesively connected to one end 90 of filter 15. A similarly shaped end cap or plate 92 is connected to an opposite end 94 of the filter. The operational significance of the shaft and end caps will be described in greater detail with respect to FIG. 9. The shape of the filter is static or constant, but the shape defines multiple filtering profiles, as hereinafter described.

Still referring to FIG. 6, filter 15 has a general bowtie or hourglass shape. In this regard, each of the ends 90, 94 of filter 15 has a diameter that is greater than the diameter of the body 96 that extends between each of the ends. Body 96, however, is uniquely designed to have a depression defined by surface 98 as well as a second depression defined by surface 100. In the embodiment illustrated in FIG. 6, each of the depressions is positioned orthogonally from one another. The orthogonal placement of the depressions illustrates only one example of how the body 96 of filter 15 may be constructed. As such, the depressions may be formed in the body 96 of filter 15 so as to be more acutely or obtusely defined with respect to one another. Further, the body may be constructed to have multiple depressions including more than two depressions. As will be discussed in greater detail below, the depressions define the shape of filter 15 such that a multitude of filtering profiles is possible.

Figure 7:
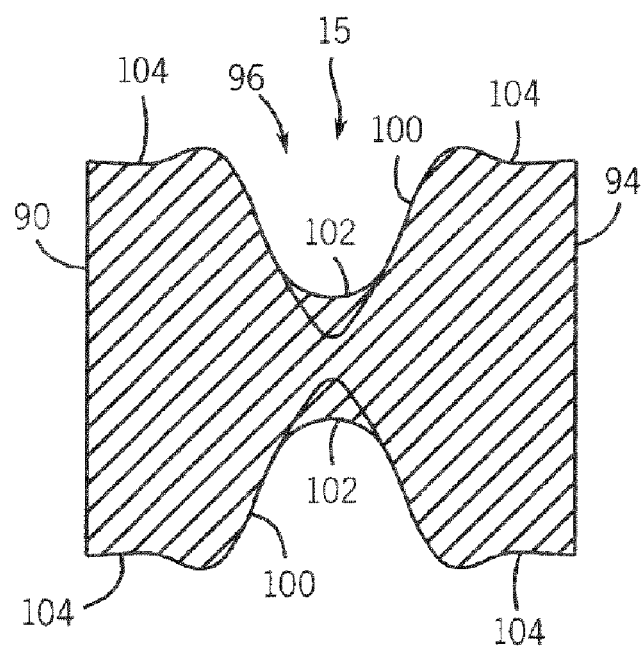
FIG. 7 is a cross-sectional view taken lengthwise along the filter shown in FIG. 6.

Refening now to FIG. 7, a cross-sectional view of filter 15 illustrating a first filtering profile is shown. It is readily apparent in FIG. 7 that the body 96 of filter 15 extending between ends 90 and 94 includes a relatively steep depression defined by surface 100. In this regard, a minimum body diameter is formed at the base 102 of the depression. The filtering profile of filter 15 that results from the orientation illustrated in FIG. 7 is particularly well suited for pre-patient filtering of an x-ray beam that is being projected toward the patient from a projection source generally positioned at a side of the patient, i.e. when the patient has the thickest cross-section. That is, since a patient generally has a thicker cross-section in the x-direction than in the y-direction, when lying on a patient table, filter 15 is designed such that the filtering profile illustrated in FIG. 7 is presented when x-rays are projected toward a thicker patient cross-section. Simply, filter 15 is designed such that x-rays received at surfaces 104 of filter 15 undergo greater filtering than the x-rays received at surfaces 98, 100. This variation in filtering power throughout the filter ensures that the sum of the x-ray beam lengths is uniform at the x-ray detector array interface.

Figure 8:
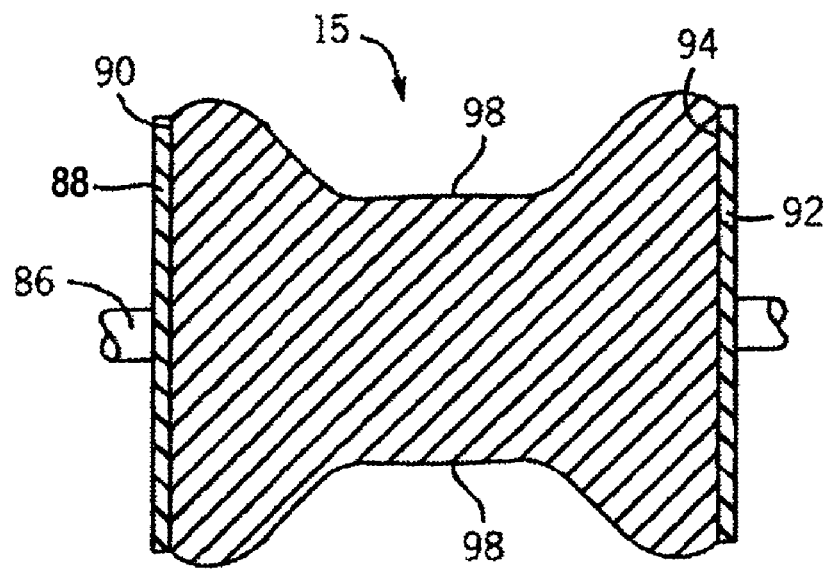
FIG. 8 is a cross-sectional view taken lengthwise along the filter showing FIG. 6 and orthogonal to the cross-sectional view shown in FIG. 7.

Referring now to FIG. 8, another cross-sectional view of filter 15 is shown that is orthogonal to the cross-sectional view illustrated in FIG. 7. In this regard, the filtering profile of filter 15 is defined by surface 98. Similar to the filtering profile illustrated in FIG. 7, the filtering profile of FIG. 8 also has a relative bowtie or hourglass shape, but the depression formed by surface 98 is less steep than the depression illustrated in FIG. 7. In this regard, the filtering profile illustrated in FIG. 8 is particularly well suited for presentation in the x-ray fan beam path when the x-ray source is projecting x-rays toward a patient from a position generally above the patient, i.e. when the patient has the thinnest cross-section. Because patients are generally flat and thin in the x-direction when positioned face-up on a patient table, the filtering profile illustrated in FIG. 8 is also relatively flat. That is, filter 15 is designed to provide less varying filtering across its width but less filtering of the fan beam when the filtering profile illustrated in FIG. 8 is presented in the x-ray beam path.

Figure 9:
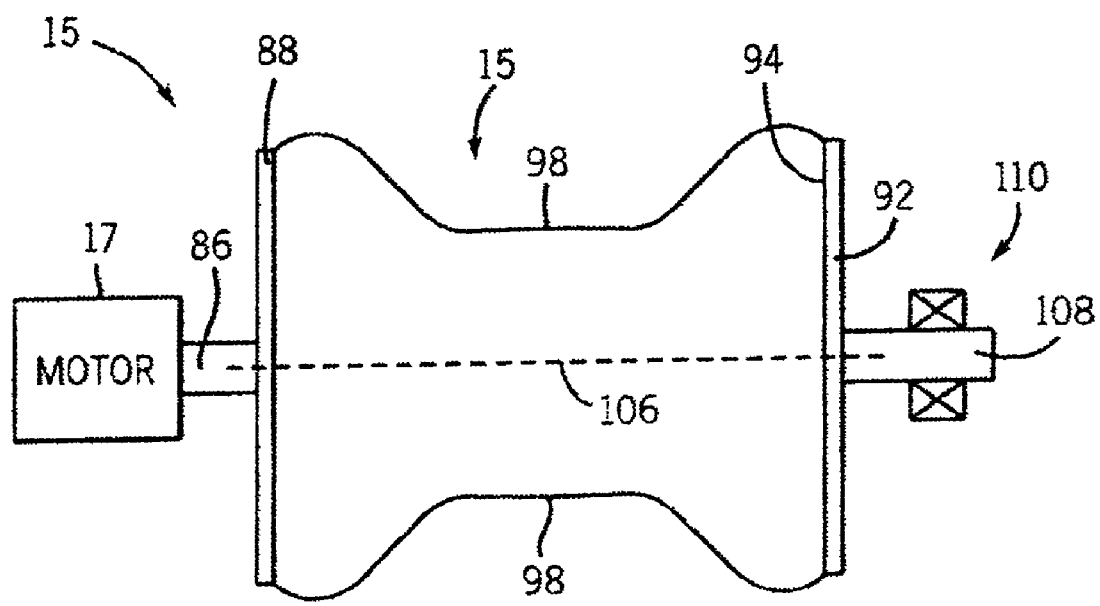
FIG. 9 is a schematic view of the pre-patient filter shown in FIG. 6 connected to a motor and a bearing assembly.

Refening now to FIG. 9, a schematic representation of the patient filter 15 is shown connected to a motor or other drive assembly 17. As indicated previously, filter 15 is positioned within the gantry of the CT system and is designed to rotate with the gantry around the patient or other scan subject during data acquisition. However, filter 15 is also constructed to spin or rotate about its lengthwise axis generally referenced 106 such that more than one filtering profile, such as those illustrated in FIGS. 7 and 8, may be presented in the x-ray beam path as the filter rotates around the patient. Accordingly, motor 17 is connected to an end cap or plate 88 that is affixed to an end of filter 15. On an opposite end, plate 92 is connected to the filter and also has a shaft 108 that is connected to a bearing assembly 110. Motor 17 is designed to rotate shaft 86 in conjunction with a bearing assembly 110 so that filter 15 is caused to spin or rotate about lengthwise axis 106 as a function of view angle of the x-ray projection source. In this regard, motor 17 may be controlled by a filter controller 33, FIG. 2, such that a steeper filtering profile, FIG. 7, is presented when the x-ray projection source is at a side of the patient. The motor may then cause filter 15 to spin or rotate about its lengthwise axis 106 such that the filtering profile illustrated in FIG. 8 is presented when the x-ray projection source is projecting x-rays from a position above the patient. One skilled in the art would readily appreciate that an encoder or other device may be incorporated with the motor such that the rotation of the gantry and the spinning of filter 15 may be synchronized. Motor 17 may also be controlled such that the filter 15 is caused to rotate or spin along its lengthwise axis uniquely for each scan session. That is, a pre-scan may be undertaken whereupon a profile of the patient is acquired and used to input data into a computer program or algorithm to control motor 17 such that the filtering profiles used throughout the imaging session are presented according to the particular contour of the particular patient undergoing the imaging session as opposed to a general control algorithm, or synchronized with table translation. Additionally, the motor may incrementally spin or rotate the filter about its lengthwise axis or provide a timed and smooth continuous rotation as a function of view angle.

Figure 10:
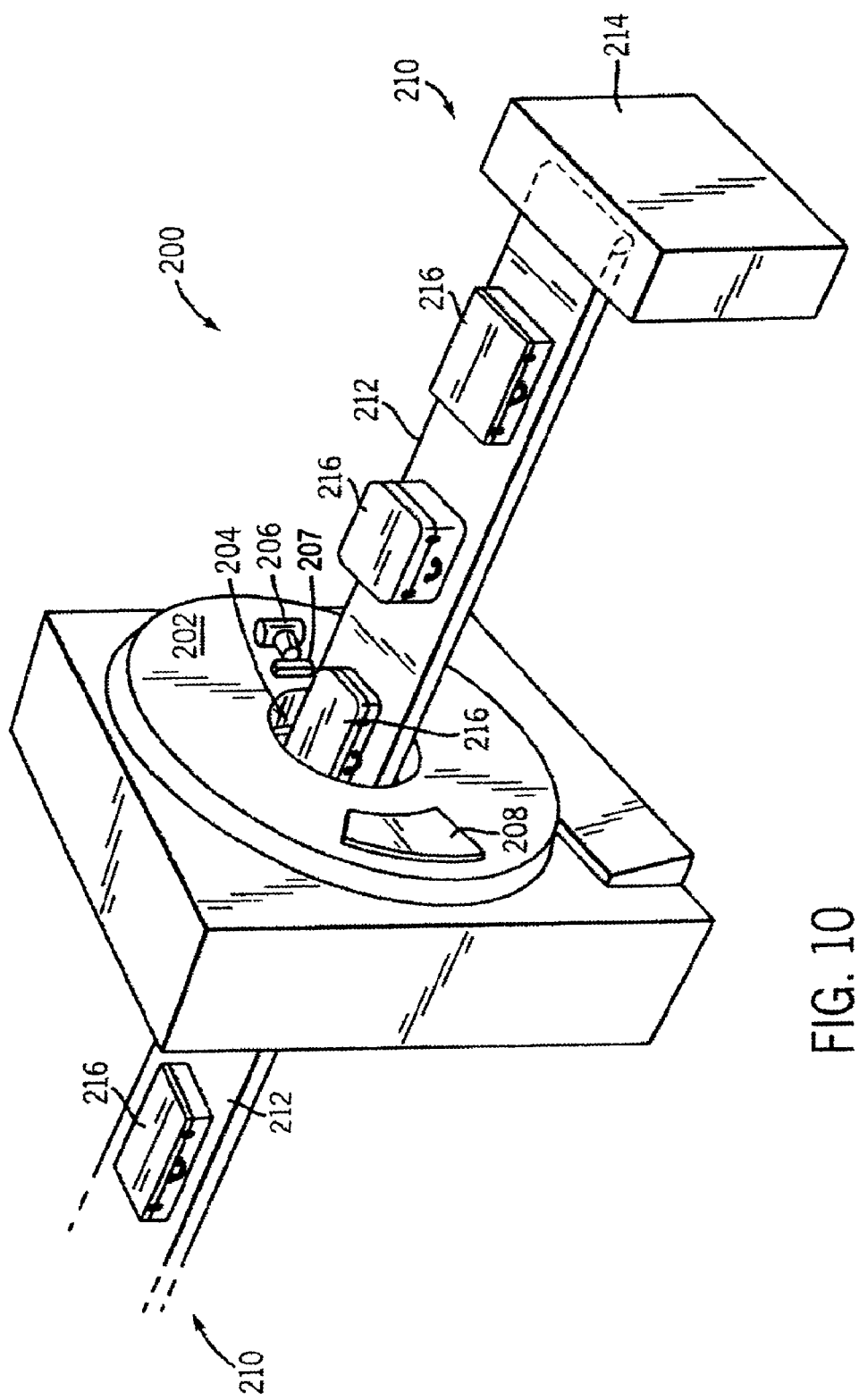
FIG. 10 is a pictorial view of a CT system for use with a non-invasive package inspection system.

Referring now to FIG. 10, package/baggage inspection system 200 includes a rotatable gantry 202 having an opening 204 therein through which packages or pieces of baggage may pass. The rotatable gantry 202 houses a high frequency electromagnetic energy source 206, a pre-subject filter 207, as well as a detector assembly 208. A conveyor system 210 is also provided and includes a conveyor belt 212 supported by structure 214 to automatically and continuously pass packages or baggage pieces 216 through opening 204 to be scanned. Objects 216 are fed through opening 204 by conveyor belt 212, imaging data is then acquired, and the conveyor belt 212 removes the packages 216 from opening 204 in a controlled and continuous manner. As a result, postal inspectors, baggage handlers, and other security personnel may non-invasively inspect the contents of packages 216 for explosives, knives, guns, contraband, etc, Therefore, in accordance with one embodiment of the present invention, a beam shaping filter for a CT imaging system includes a first end and a second end, each of which has a circular cross-section. The filter further includes a body formed of radiation beam shaping material that extends between the first end and the second end. A pair of depressions is formed in the body orthogonal from one another such that a first body diameter and a second body diameter are defined.

In accordance with another embodiment of the present invention, a CT system includes a rotatable gantry having an opening to receive a subject to be scanned as well as a rotatable high frequency electromagnetic energy projection source configured to project a high frequency electromagnetic energy beam toward the subject at af least two view angles. The rotatable pre-subject filter is also provided and has a static shape that defines at least two filtering profiles such that at a first view angle a first filtering profile filters the high frequency electromagnetic energy beam and at a second view angle a second filtering profile filters the high frequency electromagnetic energy beam. The CT system further includes a scintillator array having a plurality of scintillator cells wherein each cell is configured to detect high frequency electromagnetic energy passing through the subject as well as a photodiode array optically coupled to the scintillator array and comprising a plurality of photodiodes configured to detect light output from a corresponding scintillator cell. A data acquisition system is provided and connected to the photodiode array and configured to receive photodiode outputs which are received by an image reconstructor that is configured to reconstruct an image of the subject.

According to another embodiment of the present invention, a method of reducing x-ray exposure during CT data acquisition includes the steps of positioning a subject to be scanned in a scanning bay and projecting x-rays toward the subject from an x-ray source at a first view angle. The method also includes positioning a first profile of a multi-profile filter between x-ray source and the subject when the x-ray source is projecting x-rays at the first view angle. The method further includes the steps of spinning an x-ray source to a second view angle and projecting x-rays toward the subject from the x-ray source at the second view angle. A second profile of the multi-profile filter is then positioned between an x-ray source and the subject when the x-ray source is projecting x-rays at the second view angle.

In another embodiment, the present invention includes a pre-subject filter assembly for a CT imaging system having a detector assembly and a high frequency electromagnetic energy projection source configured to rotate about a subject during an imaging session. The filter assembly includes a beam shaping filter having a generally cylindrical shaped body defining multiple filtering profiles. The filter is constructed to rotate about an axis of rotation that extends through its body. A controller is provided to cause rotation of the filter about the axis of rotation during an imaging session to dynamically filter high frequency electromagnetic energy projected toward the subject as a function of view angle.

In another embodiment, a CT system includes a rotatable gantry having an opening to receive a subject to be scanned. A moveable high frequency electromagnetic energy projection source projects high frequency electromagnetic energy such as x-rays toward the subject at af least two view angles during an imaging session. A pre-subject filter includes a filter that is rotatable about itself relative to an axis of rotation extending the filter during the imaging session. The filter includes multiple filtering profiles. As such, the filter moves circumferentially around the subject during the imaging session but also rotates or spins relative to itself during the imaging session such that multiple filtering profiles are usable during the imaging session. The CT system further includes a scintillator array and a photodiode array that rotate synchronously with the filter and x-ray source during the imaging session. The scintillator and photodiode arrays collectively form a detector array that detects x-rays attenuated by the subject during the imaging session and outputs electrical signals indicative of the attenuation. The detector output is then input to a DAS configured to reconstruct an image of the subject. The CT system further includes a computer programmed to rotate the filter about the axis of rotation such that a first view angle a first filtering profile is presented and at a second view angle a second filtering profile is presented.

In another embodiment of the present invention, a method of reducing x-ray exposure during CT data acquisition includes positioning a subject to be scanned in a scanning bay and projecting x-rays toward the subject from an x-ray source at a first view angle. A first profile of a multi-profile filter is then positioned between the x-ray source and the subject when the x-ray source is projecting x-rays at the first view angle. The x-ray source is then rotated to a second view angle and projects x-rays toward the subject therefrom. Simultaneously therewith, the multi-profile filter is caused to rotate about an axis of rotation that extends through a length of the filter such that a second profile is positioned between the x-ray source and the subject when the x-ray source is projecting x-rays from the second view angle.

The present invention has been described in terms of the preferred embodiment, and it is recognized that equivalents, alternatives, and modifications, aside from those expressly stated, are possible and within the scope of the appending claims.

What is claimed is:

1. A pre-subject filter assembly for a CT imaging system having a detector assembly and a high frequency electromagnetic energy projection source configured to rotate about a subject during an imaging session, the filter assembly comprising:

a beam shaping filter having a body defining multiple filtering profiles, the filter rotatable about an axis of rotation that extends through the body;

wherein the beam shaping filter includes a first end and a second end, wherein the body extends between the first end and the second end and comprises a plurality of depressions to define a plurality of body diameters defining the multiple filtering profiles; and a controller to cause rotation of the beam shaping filter about the axis of rotation during an imaging session to dynamically filter high frequency electromagnetic energy projected toward the subject as a function of view angle and independent of voltage applied to the high frequency electromagnetic energy projection source.

2. The pre-subject filter assembly of claim 1 wherein the beam shaping filter has at least two filtering profiles defined orthogonally from one another, wherein the plurality of depressions comprise at least two depressions, wherein the at least two depressions define at least two body diameters defining the at least two filtering profiles defined orthogonally from one another, wherein the at least two depressions are positioned orthogonally from one another.

3. The pre-subject filter assembly of claim 2 wherein a first filtering profile of the at least two filtering profiles defines a maximum filtering profile and a second filtering profile of the at least two filtering profiles defines a minimum filtering profile, and wherein each filtering profile is defined by at least one of a geometry or a composition of the beam shaping filter.

4. The pre-subject filter assembly of claim 3 wherein the beam shaping filter includes a varying filter profile continuum connecting the first filtering profile to the second filtering profile.

5. The pre-subject filter assembly of claim 1 further comprising a pair of end caps, each of which is connected to a respective one of the first and second ends of the beam shaping filter, one end cap having a drive shaft connectable to a motor and the other end cap having a drive shaft connectable to a bearing assembly.

6. The pre-subject filter assembly of claim 1 wherein the beam shaping filter includes a bowtie filter.

7. The pre-subject filter assembly of claim 1 wherein the beam shaping filter includes a first filtering profile that has a maximum point and a minimum point and a second filtering profile has a maximum point and a minimum point, wherein a slope between the maximum point and the minimum point of the first filtering profile is larger than a slope between the maximum point and the minimum point of the second filtering profile, and wherein the controller is further configured to present the first filtering profile in a path of high frequency electromagnetic energy when the subject has a first cross-section and to present the second filtering profile in a path of high frequency electromagnetic energy when the subject has a second cross-section, the first cross-section being narrower and thicker than the second cross-section.

8. The pre-subject filter assembly of claim 1 wherein the plurality of depressions comprises a first depression and a second depression that are formed in the body so as to be acutely or obtusely defined with respect to one another and to define first and second body diameters, of the plurality of body diameters, defining first and second filtering profiles, of the multiple filtering profiles.

9. A CT system comprising:
a rotatable gantry having an opening to receive a subject to be scanned;
a movable high frequency electromagnetic energy projection source configured to project a high frequency electromagnetic energy beam toward the subject at least two view angles;
a movable pre-subject filter having a beam shaping filter that is rotatable about itself relative to an axis of rotation extending through the beam shaping filter during an imaging session, the beam shaping filter having a first end and a second end, the first end having a motor assembly connected thereto and the second end having a bearing assembly connected thereto, such that the motor assembly and bearing assembly, when commanded, cause the beam shaping filter, which has multiple filtering profiles, to rotate about the axis of rotation that is defined by a length of the beam shaping filter that is generally perpendicular to the energy beam that is projected toward the subject;
wherein the beam shaping filter includes a body that extends between the first end and the second end and comprises a plurality of depressions to define a plurality of body diameters defining the multiple filtering profiles;
a scintillator array having a plurality of scintillator cells wherein each cell is configured to detect high frequency electromagnetic energy passing through the subject;
a photodiode array optically coupled to the scintillator array and comprising a plurality of photodiodes configured to detect light output from a corresponding scintillator cell;
a data acquisition system (DAS) connected to the photodiode array and configured to receive the photodiode outputs;
an image reconstructor connected to the DAS and configured to reconstruct an image of the subject from the photodiode outputs received by the DAS; and
a computer programmed to rotate the beam shaping filter about the axis of rotation such that at a first view angle a first filtering profile filters the high frequency electromagnetic energy beam and at a second view angle a second filtering profile filters the high frequency electromagnetic energy beam.

10. The CT system of claim 9 wherein the beam shaping filter includes a bowtie filter designed to reduce high frequency electromagnetic energy dosage to the subject as a function of projection source view angle.

11. The CT system of claim 9 wherein the first filtering profile has a maximum point and a minimum point and the second filtering profile has a maximum point and a minimum point, and wherein a slope between the maximum point and the minimum point of the first filtering profile is larger than that between the maximum point and the minimum point of the second filtering profile.

12. The CT system of claim 11 wherein the computer is further programmed to present the first filtering profile when the high frequency electromagnetic energy source is projecting high frequency electromagnetic energy toward a thickest cross-section of the subject.

13. The CT system of claim 12 wherein the computer is further programmed to present the second filtering profile when the high frequency electromagnetic energy source is projecting high frequency electromagnetic energy toward a thinnest cross-section of the subject.

14. The CT system of claim 9 wherein the first view angle is orthogonal of the second view angle, wherein the plurality of depressions comprise first and second depressions, wherein the first and second depressions define first and second body diameters defining the first and second filtering profiles, wherein the first and second body diameters define the first and second filtering profiles orthogonally from one another, wherein the first and second depressions are positioned orthogonally from one another.

15. The CT system of claim 9 incorporated into at least one of a medical imaging system and a parcel inspection apparatus.

16. A method of reducing x-ray exposure during CT data acquisition comprising the steps of:

positioning a subject to be scanned in a scanning bay;

positioning a first profile of a multi-profile, beam shaping filter between an x-ray source and the subject when the x-ray source is projecting x-rays at a first view angle, wherein the multi-profile, beam shaping filter includes a first end, a second end, and a body that extends between the first end and the second end and comprises a plurality of depressions to define a plurality of body diameters defining multiple filtering profiles that comprise the first profile and a second profile;

projecting x-rays in an x-ray beam toward the subject from the x-ray source at the first view angle;

rotating the x-ray source to a second view angle;

positioning and rotating the multi-profile, beam shaping filter about an axis of rotation that extends through a length of the multi-profile, beam shaping filter and perpendicular to the x-ray beam such that the second profile of the multi-profile, beam shaping filter is positioned between the x-ray source and the subject when the x-ray source is projecting x-rays at the second view angle; and projecting x-rays in an x-ray beam toward the subject from the x-ray source at the second view angle.

17. The method of claim 16 wherein the first profile is orthogonal to the second profile, wherein the plurality of depressions comprise first and second depressions, wherein the first and second depressions define first and second body diameters defining the first and second profiles, wherein the first and second body diameters define the first and second profiles orthogonally from one another, wherein the first and second depressions are positioned orthogonally from one another.

18. The method of claim 16 wherein the second profile has a rate change between a maximum filtering point and a minimum filtering point that is less than that between a maximum filtering point and a minimum filtering point of the first profile.

19. The method of claim 18 wherein the first view angle corresponds to a position generally adjacent a side of the subject and the second view angle corresponds to a position generally above the subject.

20. The method of claim 16 further comprising the step of rotating the multi-profile, beam shaping filter about the axis of rotation synchronously with rotation of the x-ray source around the subject.

* * * * *